(12) United States Patent
Rasselkorde et al.

(10) Patent No.: US 9,575,034 B2
(45) Date of Patent: Feb. 21, 2017

(54) METHOD AND SYSTEM FOR IMMERSION ULTRASOUND INSPECTION INCLUDING WITHIN DOWNWARDLY OPENING CAVITIES

(71) Applicant: Siemens Energy, Inc., Orlando, FL (US)

(72) Inventors: El Mahjoub Rasselkorde, Monroeville, PA (US); Michael F. Fair, Oakmont, PA (US); Francisco J. Jaimes, Jeannette, PA (US); Waheed A. Abbasi, Murrysville, PA (US); James A. Bauer, Gibsonia, PA (US)

(73) Assignee: SIEMENS ENERGY, INC., Orlando, FL (US)

( * ) Notice: Subject to any disclaimer, the term of this patent is extended or adjusted under 35 U.S.C. 154(b) by 360 days.

(21) Appl. No.: 14/206,287

(22) Filed: Mar. 12, 2014

(65) Prior Publication Data

US 2015/0260690 A1 Sep. 17, 2015

(51) Int. Cl.
| | |
|---|---|
| *G01N 29/26* | (2006.01) |
| *G01N 29/22* | (2006.01) |
| *G01N 29/265* | (2006.01) |
| *G01N 29/28* | (2006.01) |
| *G01N 29/44* | (2006.01) |

(52) U.S. Cl.
CPC .......... *G01N 29/262* (2013.01); *G01N 29/225* (2013.01); *G01N 29/265* (2013.01); *G01N 29/28* (2013.01); *G01N 29/4472* (2013.01); *G01N 2291/0258* (2013.01); *G01N 2291/101* (2013.01); *G01N 2291/2693* (2013.01)

(58) Field of Classification Search
CPC ............ G01N 29/265; G01N 29/28226; G01N 29/225; G01N 29/262; G01N 29/26; G01N 29/4472; G01N 29/4454; G01N 29/4445; G01N 2291/2636; G01N 2291/106; G01N 2291/101; G01N 2291/2693; G01N 2291/044; G01N 2291/0234

USPC .......... 376/252, 249; 73/623, 629, 625, 626, 73/641, 602, 622, 620, 627; 702/39
See application file for complete search history.

(56) References Cited

U.S. PATENT DOCUMENTS

| | | | | |
|---|---|---|---|---|
| 4,597,294 A | * | 7/1986 | Brill, III | F22B 37/003 376/252 |
| 4,757,716 A | * | 7/1988 | Nottingham | F01D 21/003 73/623 |
| 5,194,215 A | * | 3/1993 | Nachbar | G21C 17/017 165/11.2 |

(Continued)

FOREIGN PATENT DOCUMENTS

EP 0 251 698 1/1988

*Primary Examiner* — Lisa Caputo
*Assistant Examiner* — Nathaniel T Woodward (57) ABSTRACT

Immersion ultrasonic NDE is performed within cavities of inanimate objects, having downwardly directed openings, such as for in situ inspection of steam inlet sleeves and steam inlet necks within steam turbine housings. A shaft assembly has one or more single angle or phased array ultrasonic probes that are affixed on an upstream or distal end. An inflatable bladder is affixed to the shaft on a proximal end of the shaft assembly downstream the ultrasonic probe(s). The shaft is inserted into the cavity opening, and the bladder is inflated to form a fluid tight seal against the cavity. Immersion fluid is introduced upstream the bladder in the volume occupied by the probes. Immersion ultrasonic inspection of the object is then performed.

12 Claims, 4 Drawing Sheets

(56) References Cited

U.S. PATENT DOCUMENTS

| | | | | |
|---|---|---|---|---|
| 5,268,940 | A | * | 12/1993 | Roseveare ............ G21C 17/003 376/249 |
| 5,371,767 | A | * | 12/1994 | Pirl ...................... B23K 26/282 219/121.63 |
| 5,396,800 | A | * | 3/1995 | Drinon ................. G01N 27/902 324/221 |
| 5,611,948 | A | * | 3/1997 | Hawkins ................ B65H 63/00 219/121.63 |
| 6,487,922 | B1 | * | 12/2002 | Bauer ................. G01N 29/225 356/3.03 |
| 6,880,379 | B2 | * | 4/2005 | Hedberg .................. G01N 3/30 702/38 |
| 6,886,407 | B1 | | 5/2005 | Fredenberg |
| 7,921,717 | B2 | * | 4/2011 | Jackson ................ G03B 42/06 600/443 |
| 8,166,821 | B2 | * | 5/2012 | Killian ................ G01N 27/902 73/601 |
| 8,312,771 | B2 | * | 11/2012 | Randall ................ A61B 8/4483 600/437 |
| 8,438,929 | B2 | | 5/2013 | Metala et al. |
| 2009/0158850 | A1 | * | 6/2009 | Alleyne ............... G01N 29/221 73/623 |

* cited by examiner

METHOD AND SYSTEM FOR IMMERSION ULTRASOUND INSPECTION INCLUDING WITHIN DOWNWARDLY OPENING CAVITIES

BACKGROUND OF THE INVENTION

1. Field of the Invention

The invention relates to immersion ultrasonic non-destructive evaluation within internally defined cavities of inanimate test objects, including in downwardly facing cavities by a test system and test methods that block the cavity opening so that ultrasonic immersion fluid remains in the cavity during the inspection procedure. Embodiments of the immersion ultrasound inspection system and test methods described herein are suitable for immersion inspection of test objects with inclined or vertical bottom opening cavities that otherwise are not capable of retaining ultrasonic testing immersion fluid. Embodiments of the methods and apparatus of the invention are suitable for in situ inspection of steam turbine engine steam inlets, including steam inlet sleeve necks, while the steam inlet remains in situ within a steam turbine upper housing.

2. Description of the Prior Art

Figure 1:
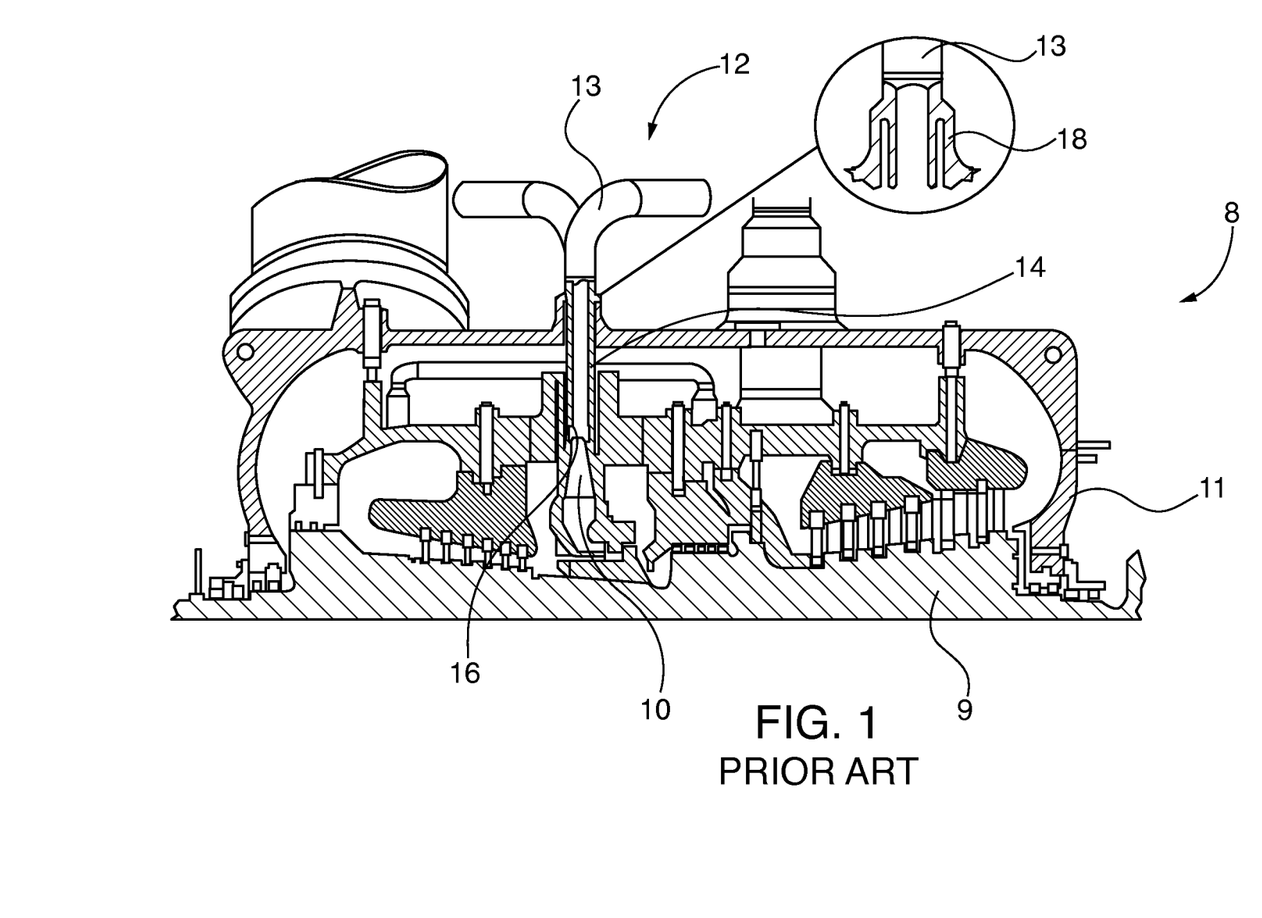
FIG. 1 is a quarter elevational schematic view of a known steam turbine engine, having a downwardly directed steam inlet sleeve with a downwardly directed outlet open cavity, showing an exemplary steam inlet and row of turbine blades on the engine rotor.

FIG. 1 shows a known High Pressure (HP) and HP/Intermediate Pressure (IP) steam turbine engine 8, having a rotating rotor 9 that includes a row of turbine blades 10. The turbine engine 8 has an upper housing 11 that includes a plurality of steam inlets 12. An inlet sleeve 14 used in the steam turbine directs steam from the inlet and its piping, 12, including the elbow portion 13, through the outer and inner cylinder walls of the upper housing 11. The steam inlet sleeve downstream outlet portion 16 adjoins a nozzle chamber for directing the pressurized steam onto the turbine blades 10. As shown in greater detail in FIGS. 2 and 3, the inlet sleeve 14 is essentially a cantilevered tubular structure fixed at the upstream inlet sleeve neck 18 adjoining the elbow portion 13, while the outlet portion 16 is only restrained by a friction interlocked sealing device proximal the nozzle chamber/turbine blades 10. Steam flow in the steam inlet structure 12 can induce vibration in the inlet sleeve 14, especially if there is a loss of frictional damping between the sleeve and the sealing device. Either constant or intermittent vibration of the sleeve 14 can result in a fatigue crack at the trepan fillet radius of the inlet sleeve neck 18. These fatigue cracks, if undetected, can result in a through wall failure of the sleeve 14 and eventually force the unit out of service.

Frequent NDE inspection and early detection is required to preclude such events. For that reason, the sleeves are inspected periodically during scheduled maintenance service outages and replaced if cracks are present. During inspection the steam turbine engine 10 upper housing is removed and elevated on a service pad, so that inspectors can insert NDE inspection instruments into the upwardly facing inlet sleeve downstream outlets 16 of the steam inlet sleeves 14. The sleeve necks 18 are inspected by inserting NDE test instruments up the inclined vertically oriented steam sleeves 14. Known ultrasonic inspection methods for steam inlet sleeve neck 18 NDE involve cleaning the inner surface of the generally tubular steam sleeve proximal the sleeve neck 18 and performing contact-type ultrasonic inspection of the neck structure by directing ultrasonic waves through the neck with either single angle or phased array transducers that are oriented relative to the neck with ultrasonically transparent orientation wedges. It is difficult and inconvenient to clean the steam sleeve 14 internal surfaces, align transducer orientation wedges at an extended distance upstream the sleeve 14 and then maneuver the wedges and transducer probe to capture a satisfactory inspection image. Also surface texture or physical condition of some cavities makes them difficult to establish satisfactory direct contact with the transducer orientation wedge that is necessary to obtain a satisfactory inspection image.

SUMMARY OF THE INVENTION

A suggested object of embodiments of the invention is to perform ultrasonic NDE inspections within cavities of inanimate objects, including cavities having inclined or vertically oriented, downwardly openings, without the need to clean or otherwise prepare the cavity inspection surface or without the need to utilize direct contact transducer orientation wedges.

This object is achieved in one or more embodiments of the invention by systems and methods of immersion ultrasonic NDE within cavities of inanimate objects, including cavities having inclined or vertically oriented, downwardly openings. Embodiments of the invention include a shaft assembly to which one or more single angle or phased array ultrasonic probes is affixed on an upstream or distal end. An inflatable bladder is affixed to the shaft on a proximal end of the shaft assembly downstream the ultrasonic probe(s). The shaft is inserted into the cavity opening, with the probes aligned with the area of inspection interest and the bladder is inflated to form a fluid tight seal against the cavity. Immersion fluid is introduced upstream the bladder in the volume occupied by the probes, the bladder preventing the fluid from leaking out of the cavity opening. The probe(s) can now transmit an ultrasonic wave through the fluid in the cavity and into the inanimate object, receive the responsive echo ultrasonic wave, and convert the received wave into a test data stream using known ultrasonic testing instrumentation. A motion control system, coupled to the ultrasonic probe and the shaft assembly, selectively moves the probe relative to the cavity and generates transducer position data. A controller interfacing with the ultrasonic testing instrumentation and the motion control system receives the processed test data and the transducer position data, and creates a model of the inspected inanimate object that identifies potential location and size characteristics the object. The inspection system and methods of embodiments of the invention are suitable for in situ inspection of steam inlet sleeves, including steam inlet necks within steam turbine housings.

Embodiments of the invention feature an immersion based ultrasonic inspection system for non-destructive evaluation of inanimate objects defining a cavity. The system has a shaft assembly for insertion into a cavity of an inanimate object. An immersion ultrasonic probe is coupled to an upstream distal end of the shaft assembly, for transmitting an ultrasonic wave through fluid in the cavity surrounding the probe into the inanimate object, receiving a responsive echo ultrasonic wave, and converting the received wave into a test data stream. An inflatable bladder is coupled to a downstream proximal end of the shaft assembly, for insertion into the cavity and for subsequent inflation to establish a fluid tight seal within the cavity upstream the bladder, facilitating immersion of the upstream ultrasonic probe. A motion control system is coupled to the ultrasonic probe and the shaft assembly, for selectively moving the probe relative to the cavity and generating transducer position data. An ultrasonic testing instrument interfaces with the probe, for receiving and processing the test data stream into processed data in order to identify potential defect location and size characteristics. A controller interfaces with the ultrasonic testing instrument and the motion control system, for receiving the processed data and the transducer position data, and for creating a model of the inspected inanimate object that identifies potential location and size characteristics therein.

Other embodiments of the invention feature methods for immersion based ultrasonic non-destructive evaluation of an inanimate object defining a cavity. An ultrasonic inspection system is provided, having a shaft assembly for insertion into a cavity of an inanimate object; an immersion ultrasonic probe or probes are coupled to an upstream distal end of the shaft assembly, for transmitting an ultrasonic wave through fluid in the cavity surrounding the probe into the inanimate object, receiving a responsive echo ultrasonic wave, and converting the received wave into a test data stream. The probe(s) is/are immersion-type single angle or phased array probes. An inflatable bladder is coupled to a downstream proximal end of the shaft assembly, for insertion into the cavity and for subsequent inflation to establish a fluid tight seal within the cavity upstream the bladder, facilitating immersion of the upstream ultrasonic probe. A motion control system is coupled to the ultrasonic probe and the shaft assembly, for selectively moving the probe relative to the cavity and generating transducer position data. An ultrasonic testing instrument interfaces with the probe, for receiving and processing the test data stream into processed data in order to identify potential defect location and size characteristics. A controller is provided, which interfaces with the ultrasonic testing instrument and the motion control system, for receiving the processed data and the transducer position data, and for creating a model of the inspected inanimate object that identifies potential location and size characteristics in it. When performing the inspection method the distal end of the shaft assembly, along with the probe and the bladder, is inserted into a cavity of an inspected inanimate object, such as a steam inlet sleeve. The bladder is inflated, which establishes a fluid tight seal within the cavity upstream of the bladder. Fluid is introduced upstream of the inflated bladder, immersing the probe in the fluid. The probe transmits an ultrasonic wave through the fluid in the cavity surrounding the probe into the inanimate test object and receives a responsive echo ultrasonic wave. The probe converts the received wave into a test data stream with the probe. The probe is moved relative to the cavity with the motion control system while performing the ultrasonic wave transmitting echo wave receiving and generating probe position data, for correlation with the test data stream associated with each such position. The test stream data are received and processed by the ultrasonic testing instrument, in order to identify potential defect location and size characteristics. A model of the inspected inanimate object is created with the controller. The model identifies potential location and size characteristics within the test object using the processed data and the transducer position data.

Additional embodiments of the invention feature a method for immersion based ultrasonic non-destructive evaluation of a sleeve neck of a steam turbine engine steam inlet. The inlet has a generally tubular steam inlet sleeve with a distal open outlet end for introduction of pressurized steam to a row of turbine blades in the engine and a proximal end coupled to an upstream elbow, with the sleeve neck intermediate the elbow and the open outlet end. The evaluation method is performed by providing an ultrasonic inspection system having a shaft assembly for insertion into an inlet sleeve outlet end. An immersion ultrasonic probe is coupled to an upstream distal end of the shaft assembly, for transmitting an ultrasonic wave through fluid in the cavity surrounding the probe into sleeve neck, receiving a responsive echo ultrasonic wave, and converting the received wave into a test data stream. An inflatable bladder is coupled to a downstream proximal end of the shaft assembly, for insertion into inlet sleeve and for subsequent inflation to establish a fluid tight seal within the inlet sleeve upstream the bladder, facilitating immersion of the upstream ultrasonic probe. A motion control system is coupled to the ultrasonic probe and the shaft assembly, for selectively moving the probe relative to the inlet sleeve neck and generating transducer position data. An ultrasonic testing instrument interfaces with the probe, for receiving and processing the test data stream into processed data, in order to identify potential defect location and size characteristics in the sleeve neck. A controller interfaces with the ultrasonic testing instrument and the motion control system, for receiving the processed data and the transducer position data, and for creating a model of the inspected sleeve neck that identifies potential location and size characteristics therein. Using the provide inspection system, method is performed by inserting the distal end of the shaft assembly, along with the probe and the bladder, into an inlet sleeve, inflating the bladder and establishing a fluid tight seal within the inlet sleeve upstream of the bladder. Fluid is introduced upstream the inflated bladder, immersing the probe in the fluid. An ultrasonic wave is transmitted through the fluid in the cavity surrounding the probe into the sleeve neck. A responsive echo ultrasonic wave is received with the probe, where it is converted into a test data stream. The probe is moved relative to the sleeve inlet neck while performing the ultrasonic wave transmitting echo wave receiving and generating probe position data for correlation with the test data stream associated with each such position. The ultrasonic testing instrument receives and processes the test data stream into processed data, in order to identify potential defect location and size characteristics in the sleeve neck. A model of the inspected sleeve neck is created by the controller, using the processed data and the transducer position data. The model identifies potential location and size characteristics of defects within the inlet neck or other inspected locations.

The respective objects and features of the invention embodiments described herein may be applied jointly or severally in any combination or sub-combination by those skilled in the art.

BRIEF DESCRIPTION OF THE DRAWINGS

Embodiments of the invention can be understood by considering the following detailed description in conjunction with the accompanying drawings, in which.

To facilitate understanding, identical reference numerals have been used, where possible, to designate identical elements that are common to the figures.

DETAILED DESCRIPTION

Figure 2:
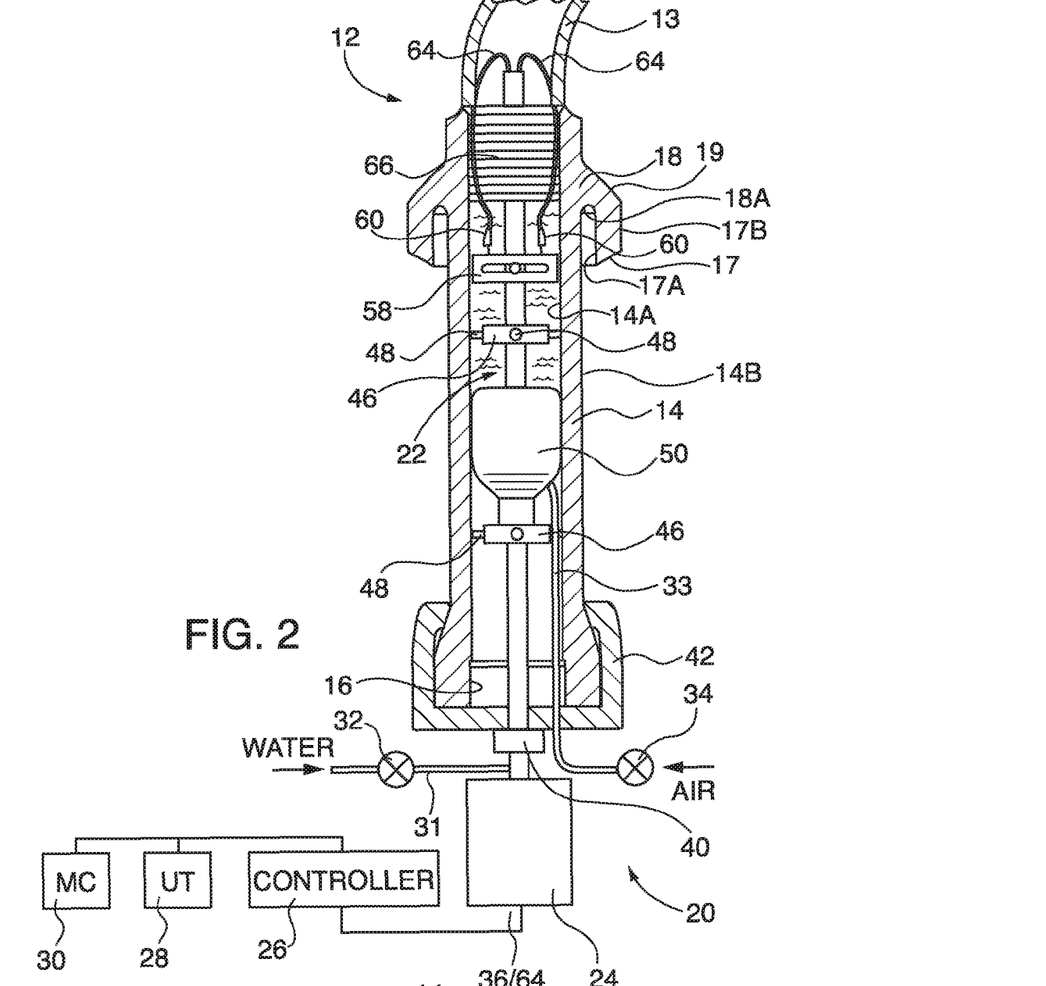
FIG. 2 is an elevational view of the immersion ultrasound inspection system in accordance with an embodiment of the invention used for in situ inspection of a steam inlet sleeve neck.
Figure 3:
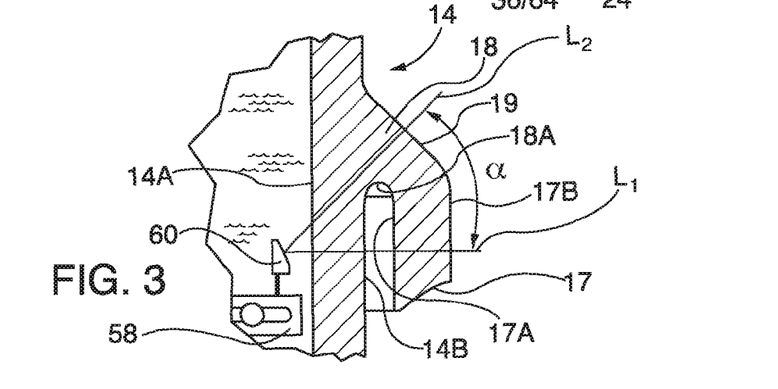
FIG. 3 is a detailed view of the steam inlet sleeve neck of FIG. 2, showing an inspection scanning zone of an ultrasonic phased array immersion probe.

After considering the following description, those skilled in the art will realize that the teachings of embodiments of the invention can be utilized in immersion ultrasonic NDE within cavities of inanimate objects, having downwardly directed openings, such as for in situ inspection of steam inlet sleeves and steam inlet necks within steam turbine housings. For brevity, application of the apparatus and methods of the invention to perform a NDE inspection of a steam turbine sleeve 14 are discussed herein, but it is understood that they can be applied to other types of test object cavities. Referring to FIGS. 2; and 3, the steam turbine inlet sleeve 14 includes an inlet-sleeve inner wall 14A, and an inlet-sleeve outer wall 14B. A circumferential sleeve 17 has a circumferential-sleeve inner wall 17A that is circumferentially spaced, in opposing relationship with the outer wall 14B of the inlet sleeve 14, with these opposing walls bridged by an adjoining surface forming a trepan fillet radius 18A of the sleeve neck 18. A sleeve slope 19, formed in the sleeve neck 18, above the trepan fillet radius surface, bridges the inlet-sleeve outer wall 14B and the circumferential-sleeve outer wall 17B. The circumferential sleeve 17 is coupled to the upper housing 11.

Referring generally to FIGS. 2-5, the immersion ultrasonic inspection system 20 includes an inspection tool 22 shaft assembly, which has one or more known, conventional single angle or phased array ultrasonic probes 60 that is/are affixed on an upstream or distal end. An inflatable bladder 50 is affixed on a proximal end of the shaft assembly downstream the ultrasonic probe(s) 60. The shaft assembly 22 is inserted into the opening or outlet 16 of the steam inlet sleeve 14 internal cavity, and the bladder 50 is inflated to form a fluid tight seal against the sleeve's interior cavity. Immersion fluid is introduced upstream the bladder 50 in the volume occupied by the probes 60 and then the ultrasonic NDE is performed. The probe or probes 60 is/are moved in the immersion fluid, such as water, using a drive unit 24 of a motion control system 30. The respective probe(s) 60 axial and circumferential positions are traced by the motion control system 30, to generate position data. The probe(s) 60 is/are first accurately moved using the motion control system drive unit 24 in the axial direction of the object to be inspected, such as an inlet sleeve 14, until an intended inspection location is reached. The probe 60 is then moved in the circumferential direction in order to scan the inlet sleeve neck 18 from 0 to 360 degree positions. Referring to FIGS. 2 and 6, if two probes 60 oriented at oppositely directed 180 degree positions, are utilized then only a 180 degree (half turn) circumferential scanning motion is needed to scan the entire 360 degrees of the sleeve 14's cavity along an area of interest. As shown in FIGS. 2 and 3, the area of interest for scanning is a volume of the neck portion 18, which is designated by the angle α. A lower axial extreme of the area of interest in the scanned volume, designated by the lower line $L_1$, which represents the extreme lower boundary or beam angle of the scanned volume, includes the outer wall 14B of the inlet sleeve, the trepan fillet radius 18A, and circumferential-sleeve outer wall 17B. An upper axial extreme of the area of interest's scanned volume, designated by the upper line $L_1$, which represents the extreme upper boundary or beam angle of the scanned volume, includes the outer wall 14B of the inlet sleeve through the slope 19 the of sleeve neck 18. Thus the area of interest includes the trepan fillet radius surface 18A, and immediately adjoining portions of the inlet sleeve 14, the circumferential sleeve 17, and the slope 19.

Immersion ultrasound NDE eliminates the need to use a transducer-alignment wedge block or to prepare the cavity surface for smooth contact with the wedge block. Both surface preparation and alignment-wedge block placement are physically challenging when attempting to reach upwardly vertically from a steam sleeve 14 outlet 16 toward its distally oriented sleeve neck 18. Advantageously, scanning motion range is also reduced by use of a phased array probe 60 in immersion mode, as the need to translate the probe axially to cover the inspected volume is reduced. An exemplary phased array probe 60 advantageously steers the ultrasonic inspection transmission beam wave at different angles α, so that flaws at different orientations in the test object can be detected by the probe 60 with the received echo wave. The received echo wave is converted to test data. A typical range of the ultrasonic beam angle α is 30° to 60° to cover the axial dimension of the inspected volume area of interest, such as a steam inlet sleeve neck 18, as shown in FIG. 3. As previously described, the area of interest is bounded by lower and upper axial extremes and their corresponding lower $L_1$ and upper $L_2$ lines. The lower axial extreme $L_1$ of the scanned volume includes the outer wall 14B of the inlet sleeve, the trepan fillet radius 18A, and circumferential-sleeve outer wall 17B. The upper axial extreme $L_2$ of the scanned of the scanned volume includes the outer wall 14B of the inlet sleeve through the slope 19 the of sleeve neck 18. A typical known sleeve inlet wall thickness varies between approximately 0.5 inches to 2.0 inches (12 mm to 50 mm): thus, the beam is focused in that range of depth. The focusing of the beam at the area of interest also allows better sizing and resolution of the flaw. As previously noted, utilization of a pair of oppositely oriented phased array immersion probes 50 also reduces needed circumferential scan sweep by 50 percent, as only 180 degrees, rather than 360 degrees of circumferential sweep are needed to complete a full inspection scan of the aforementioned upper $L_2$ and lower $L_1$ bounded axial extremes of the scan volume of the area of interest within the sleeve neck 18 or other portions of the sleeve 14.

Probe test data are utilized by a known ultrasonic testing instrument 28 to generate processed data that identify potential defect location and size characteristics: for example, defect depth in the scanned volume and defect approximate size. The controller 26 utilizes the ultrasonic testing instrument 28 processed data and the motion control system 30 corresponding position data to construct a model of the inspected steam sleeve neck 18 that identifies potential defect location and size characteristics. The an exemplary controller is a known personal computer programmed to perform the sleeve neck 18 or other inspected test object modeling and output the inspection information via known human machine interface devices, such as displays or printers, or to directly connected data storage devices or data networks.

Figure 4:
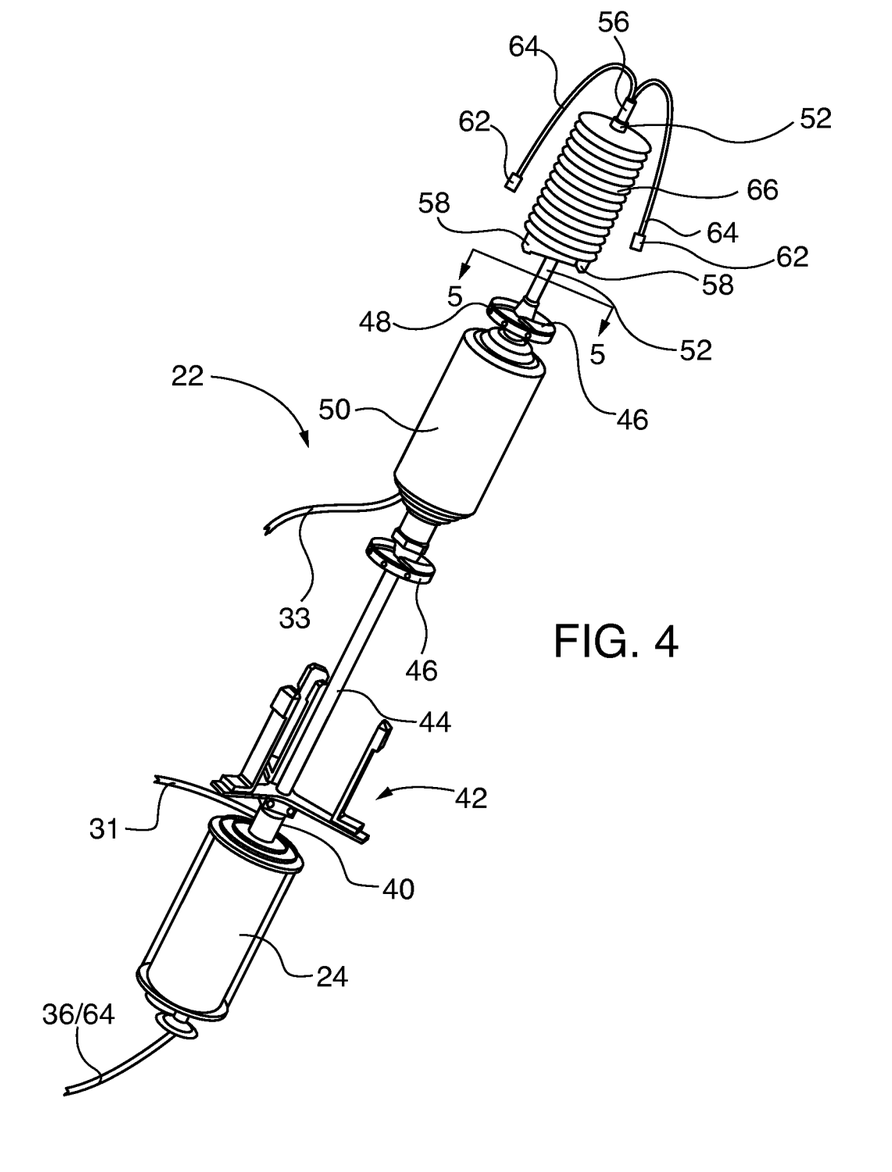
FIG. 4 is a perspective schematic view of an ultrasound shaft assembly of the ultrasound inspection system of FIG. 2.
Figure 5:
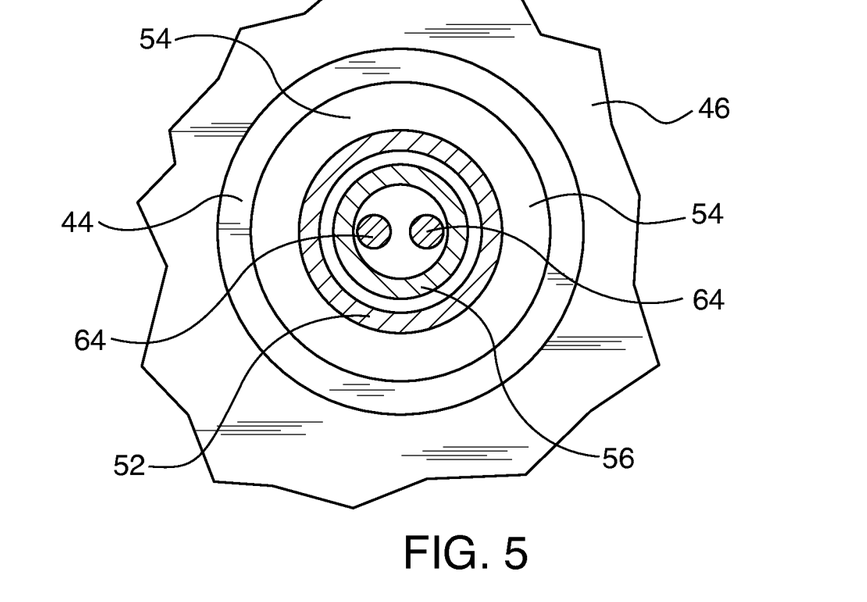
FIG. 5 is a cross sectional view of the shaft assembly of FIG. 4, taken along 5-5 thereof.
Figure 6:
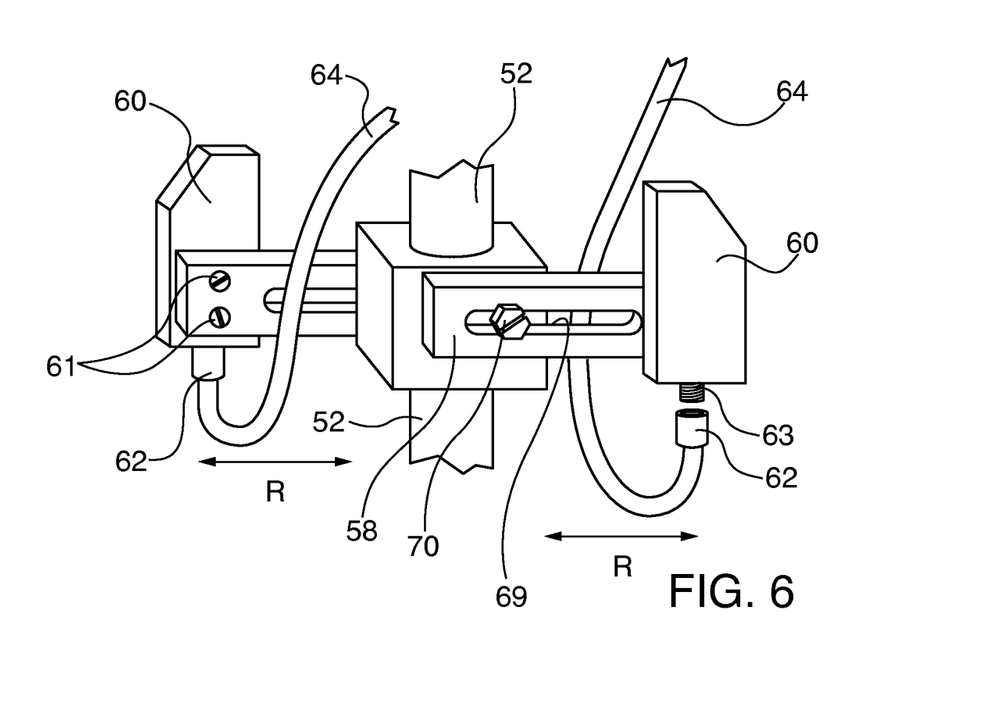
FIG. 6 is a detailed perspective view of an opposed pair of immersion ultrasound phased array probes and disconnecting couplings, in accordance with an embodiment of the invention.

Structure of the shaft assembly 22 is shown in greater detail in FIGS. 4-6. The shaft assembly 22 is coupled to the motion control drive system 24, the controller 26, the ultrasonic test instrument 28 and the motion control system 30 by the power/communications cable 36. The shaft assembly 22 is also coupled to a water supply line 31, controlled by water valve 32, for selectively introducing inspection immersion fluid in the void upstream of the bladder 50, after its inflation by air supply line 33 and air supply valve 34. The motion control drive system 24 is coupled to drive support collar 40 and inlet sleeve clamp assembly 42 by stationary outer support tube 44. The outer support tube 44 also retains a pair of centering discs 46 that in turn have radially adjustable indexing pins 48, for centering the shaft assembly within the inlet sleeve 14. The inlet sleeve clamp assembly 42 holds and maintains axial alignment of the shaft assembly 22 with the inlet sleeve 14. As shown in FIGS. 4 and 5, axially and radially displaceable motion control drive tube 52 is retained within the outer support tube 44 and is driven by the motion control drive system 24, under command of the motion control system 30.

The outer support tube 44 terminates upstream the bladder 50 and is coupled to the water supply line 33. Probe immersion water is introduced to or drained from the inlet sleeve upstream of the bladder 50 by way of the annular water jacket 54 formed between the outer support tube 44 and the motion control drive tube 52. Stationary mandrel tube 56 provides a radially restraining guide surface for the motion control drive tube 52. One or more probe clamps 58 are coupled to the motion control drive tube 52, which establish radial orientation for each corresponding ultrasound probe 60 relative to the test object (e.g., inlet sleeve neck 18). As previously mentioned, use of a pair of 180 degree opposed ultrasonic probes 60 facilitates full circumferential inspection of the inlet sleeve neck 18 with only a half turn of motion control drive tube rotation.

Each ultrasound probe 60 is coupled to a radial position clamp 58 by retention screws 61. Power and signal communication between each probe 60 and the ultrasonic inspection system 28 is provided by a fixed or removable coupling, selectively connectable transducer cable 64. Selective coupling is established by way of threaded ferrule 62 on the cable 64 and male threaded terminal 63 on the probe 60. Selective coupling of the probe 60 and cable 64 facilitates routing of the cable through the center of the mandrel tube 56, exiting out of mandrel tube distal end, as shown in FIG. 4. Other known types of known selective coupling connectors may be utilized to couple the probe 60 and cable 64. Bellows 66 constrains splashing or other propagation of immersion fluid upstream of the probes 60, such as down the distal terminal end of mandrel tube 56 toward the motion control drive system 24. Constraining the immersion fluid is also beneficial for probe 60 transmission continuity.

The use of an immersion ultrasound technique also maintains a constant transmission of the ultrasonic sound in the material test object material and eliminates the variation of the signal response due to the lack of ultrasonic wave transmission couplant control between a wedge block and the test object surface otherwise needed to perform a non-immersion ultrasonic inspection. For example, the surface condition of the inner diameter (ID) of a typical in-service steam turbine inlet sleeve 14 is usually rough. Often corrosion and scales can be found on the surface of the inlet sleeve. The use of contact probes and wedges can cause problems with interpretation of the data Immersion ultrasound procedures do not have test object inner surface condition or couplant control issues impacting test data. Wedge and contact probes ultrasound test inspection methods, including those utilizing phased array contact probes, require multiple sets of wedge profiles for different inner diameter inlet sleeves or for irregularly shaped test object inner surface profiles. There is no need to utilize wedge blocks with immersion ultrasonic inspection methods and apparatus of embodiments of the invention. The same immersion probe or multiple probes—whether single angle or phased array probes—can be used for all types of inspected object cavities by adjusting probe 60 radial spacing R, along the slot 69 in a corresponding probe clamp 58 and locking the clamp retention screw 70, without the need for contact probes and probe wedges.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A method for immersion based ultrasonic, non-destructive evaluation of an area of interest within a sleeve neck of a tubular steam inlet sleeve for a steam turbine engine, the area of interest including a portion of the sleeve neck defining a trepan fillet radius surface that is in communication with an outer wall of the inlet sleeve and an inner wall of a circumferential sleeve which is circumferentially spaced, in opposing relationship with the outer wall of the inlet sleeve, and a sleeve slope formed in the sleeve neck, above the trepan fillet radius, the sleeve slope bridging the inlet-sleeve outer wall and an outer wall of the circumferential sleeve, the method comprising:

providing a tubular steam inlet sleeve, having an outlet end, a sleeve neck, which defines a trepan fillet radius surface portion, proximate an opposite end of the sleeve, and a sleeve cavity in communication with both of said ends, the sleeve neck having an area of interest including:

the trepan fillet radius surface, in communication with both an adjoining outer wall of the inlet sleeve and an adjoining inner wall of a circumferential sleeve, with the circumferential sleeve oriented in opposing, circumferentially spaced relationship with the outer wall of the inlet sleeve, and a sleeve slope formed in the sleeve neck, above the trepan fillet radius surface, the sleeve slope bridging the inlet-sleeve outer wall and an outer wall of the circumferential sleeve;

providing an ultrasonic inspection system for inspecting the area of interest in the inlet sleeve, having:

a shaft assembly, having a shaft centerline axis, for insertion into the sleeve cavity through one of said inlet sleeve ends;

first and second phased array, immersion ultrasonic probes, respectively coupled to an upstream distal end of the shaft assembly in opposed 180 degree circumferential positions, selectively positioned radially with respect to the shaft centerline axis, for transmitting ultrasonic waves through surrounding immersion fluid and into a scan volume of the area of interest within the inlet sleeve, bounded by respective extreme upper and lower beam angles, wherein the difference between the upper and lower beam angles is between 30 to 60 degrees, relative to a radius of the shaft assembly, receiving responsive echo ultrasonic waves, and converting the received waves into a test data stream;

an inflatable bladder coupled to a downstream proximal end of the shaft assembly, for insertion into the sleeve cavity and for subsequent inflation to establish a fluid tight seal within the sleeve cavity upstream of the bladder, facilitating immersion of the first and second ultrasonic probes;

a motion control system, coupled to the first and second ultrasonic probes and the shaft assembly, for: selectively rotating the first and second ultrasonic probes circumferentially with respect to the shaft assembly and the sleeve cavity, selectively translating at least part of the shaft assembly in an axial direction that is parallel to its centerline axis and the inlet sleeve neck, and generating first and second ultrasonic probes transducer position data;

an ultrasonic testing instrument interfacing with the first and second ultrasonic probes, for receiving and processing the test data stream into processed data, in order to identify potential defect location and size characteristics within the scan volume of the scanned inlet sleeve; and a controller interfacing with the ultrasonic testing instrument and the motion control system, for receiving the processed data and the first and second ultrasonic probes respective transducer position data, and for identifying potential defect location and size characteristics within the scan volume of the area of interest of the inspected inlet sleeve;

inserting the distal end of the shaft assembly, along with the first and second ultrasonic probes and the bladder, into the inlet sleeve cavity;

aligning the respective beam angles of the first and second ultrasonic probes, so that their respective lower and upper extreme angles bound in the axial dimension the scan volume of the area of interest of the sleeve neck there between, by selectively positioning said probes radially with respect to the shaft centerline axis and axially by translating at least of the shaft assembly with the motion control system;

inflating the bladder and establishing a fluid tight seal within the inlet sleeve cavity upstream of the bladder;

introducing fluid upstream of the inflated bladder, immersing the first and second ultrasonic probes in the fluid;

transmitting with the respective first and second probes ultrasonic waves through the fluid in the cavity surrounding the probes and into the scan volume of the area of interest of the sleeve neck;

receiving responsive echo ultrasonic waves and converting the received waves into a test data stream with the respective first and second ultrasonic probes;

rotating the shaft assembly 180 degrees with the motion control system, in order to capture, collectively with both of the first and second ultrasonic probes, a full 360 degree circumferential and axial inspection scan of entire scan volume of the area of interest within the inlet sleeve neck, and generate a test data stream thereof, and generating corresponding transducer position data with the motion control system;

receiving and processing the test data stream into processed data with the ultrasonic testing instrument, in order to identify potential defect location and size characteristics in the scan volume of the area of interest within the inlet sleeve neck;

receiving the processed data and the respective transducer position data, and identifying potential defect location and size characteristics within the scan volume of the area of interest within the inlet of the sleeve neck, with the controller.

2. The method of claim 1, the provided shaft assembly comprising a pair of tubular, first and second nested shafts movable relative to each other;

the first and second ultrasonic probes and motion control system coupled to the first shaft, the probes movable axially and circumferentially relative to the cavity under control of the motion control system; and the bladder coupled to the second shaft.

3. The method of claim 2, the provided shaft assembly further comprising:

a stationary third shaft circumscribed by the first shaft, for guiding axial and radial motion of the first shaft; and the second shaft circumscribing the first shaft, defining a fluid passage there between, for introduction of probe immersion fluid upstream of the bladder.

4. The method of claim 3, the provided inspection system further comprising:

the third shaft having tubular construction, and captured therein a probe communication cable, for interfacing with the ultrasonic testing instrument;

a first coupling portion affixed to a distal end of the cable;

a second coupling portion affixed to the probe;

the first and second coupling portions selectively attachable to each other for establishing communication of the data test stream from the probe to the ultrasonic testing instrument.

5. The method of claim 1, further comprising providing inflatable bellows coupled to the shaft assembly upstream of the first and second ultrasonic probes, for inhibiting propagation of immersion fluid upstream of the probe, and inflating the bellows to establish a fluid tight seal, for retaining immersion fluid downstream thereof.

6. The method of claim 1 comprising:

orienting the tubular steam inlet sleeve vertically, so that the sleeve neck is above the outlet end thereof;

inserting the distal end of the shaft assembly upwardly into the sleeve outlet end into the sleeve cavity;

inflating the bladder to establish a fluid tight seal, for retaining immersion fluid above the bladder; and introducing immersion fluid above the bladder, immersing the first and second ultrasonic probes.

7. The method of claim 6, further comprising introducing immersion fluid above the bladder through a passage defined by the shaft assembly.

8. The method of claim 6, further comprising inhibiting propagation of immersion fluid upstream of the first and second ultrasonic probes by blocking the sleeve cavity.

9. The method of claim 8, further comprising inhibiting immersion fluid propagation with inflatable bellows coupled to the shaft assembly upstream the first and second ultrasonic probes, by inflating the bellows to establish a fluid tight seal, for retaining immersion fluid downstream thereof.

10. The method of claim 1, inspecting a generally vertically oriented sleeve neck in situ within an upper housing of a steam turbine engine, further comprising:
removing a steam turbine upper housing with a steam inlet elbow, steam inlet sleeve and sleeve neck intact, orienting the sleeve vertically, with the outlet end facing downwardly;
inserting the distal end of the shaft assembly, along with the first and second ultrasonic probes and the bladder, into the downwardly facing outlet end from under the upper housing;
inflating the bladder and establishing a fluid tight seal within the inlet sleeve above and upstream of the bladder;
introducing fluid above and upstream of the inflated bladder through a passage in the shaft assembly, immersing the first and second ultrasonic probes in the fluid;
moving the first and second ultrasonic probes axially relative to the inlet sleeve and its inlet neck with the motion control system, while performing the ultrasonic wave transmitting, echo wave receiving with each of the respective first and second ultrasonic probes, and generating probe position data for correlation with the test data stream associated with each such position; and
receiving the processed data and the respective transducer position data, and identifying potential defect location and size characteristics within the inspected inlet sleeve and its sleeve neck, with the controller.

11. The method of claim 1, further comprising:
the provided inspection system further having:
the shaft assembly having a pair of tubular, first and second nested shafts movable relative to each other;
the first and second phased array ultrasonic probes respectively coupled to the first shaft by respective first and second radial position clamps that are oriented in opposed 180 degree circumferential positions, which are selectively radially adjustable relative to each other and the inlet sleeve cavity by locking a clamp retention screw within an elongated slot formed in each of said radial position clamps;
the first and second ultrasonic probes movable axially and circumferentially relative to the sleeve neck under control of the motion control system; and
the bladder coupled to the second one of the shafts;
orienting the respective upper and lower extreme angles of the scanning angles of the first and second phased array ultrasonic probes to bound in the axial dimension the scan volume of the area of interest of the sleeve neck by selectively adjusting their radial spacing with the locking clamp retention screw, and translating the first shaft with the motion control system; and
rotating the shaft assembly 180 degrees with the motion control system, in order to capture, collectively with both of the first and second ultrasonic probes, a full 360 degree circumferential and axial inspection scan of the entire scan volume of the area of interest within the inlet sleeve neck with the inspection system.

12. The method of claim 1, further comprising:
providing first and second centering discs coupled to the shaft assembly on opposite sides of the bladder, respectively having radially adjustable indexing pins, for centering the shaft assembly within an inlet sleeve cavity;
providing an inlet sleeve clamp assembly, including radially outwardly displaceable jaws for biased contact with an interior wall of the inlet sleeve, for holding and maintaining alignment of the shaft assembly within the inlet sleeve;
adjusting the indexing pins so that the first and second centering discs center the shaft assembly within the inlet sleeve cavity during shaft assembly insertion;
inserting the shaft assembly into the inlet sleeve cavity; and
thereafter clamping the inlet sleeve clamp assembly in biased contact with the interior wall of the inlet sleeve.

* * * * *